US008377662B2

(12) United States Patent
De Ferra et al.

(10) Patent No.: US 8,377,662 B2
(45) Date of Patent: Feb. 19, 2013

(54) PROCESS FOR THE PRODUCTION OF N-ACYL-PHOSPHATIDYL-ETHANOLAMINE

(75) Inventors: Lorenzo De Ferra, Patrica (IT); Mauro Anibaldi, Patrica (IT); Ettore Ammirati, Patrica (IT)

(73) Assignee: Chemi S.p.A., Cinisello Balsamo (MI) (IT)

( * ) Notice: Subject to any disclaimer, the term of this patent is extended or adjusted under 35 U.S.C. 154(b) by 226 days.

(21) Appl. No.: 13/002,693

(22) PCT Filed: Jul. 8, 2008

(86) PCT No.: PCT/IT2008/000460

§ 371 (c)(1), (2), (4) Date: Jan. 5, 2011

(87) PCT Pub. No.: WO2010/004597

PCT Pub. Date: Jan. 14, 2010

(65) Prior Publication Data

US 2011/0111469 A1 May 12, 2011

(51) Int. Cl.
*C12P 13/00* (2006.01)

(52) U.S. Cl. .......................................... 435/128

(58) Field of Classification Search .................. 435/128; 558/194

See application file for complete search history.

(56) References Cited

U.S. PATENT DOCUMENTS

| | | | |
|---|---|---|---|
| 4,254,115 | A | 3/1981 | Dawidson et al. |
| 4,783,402 | A | 11/1988 | Kokusho et al. |
| 6,294,191 | B1 | 9/2001 | Meers et al. |

FOREIGN PATENT DOCUMENTS

| | | |
|---|---|---|
| EP | 0 122 151 | 10/1984 |
| EP | 1 048 738 | 11/2000 |
| EP | 1 482 920 | 11/2007 |
| GB | 2 051 069 | 1/1981 |
| WO | 03/068210 | 8/2003 |

OTHER PUBLICATIONS

Rondanelli, M. et al., "Administration of a dietary supplement ( N-oleyl-phosphatidylethanolamine and epigallocatechin-3-gallate formula) enhances compliance with diet in healthy overweight subjects: a randomized controlled trial" British Journal of Nutrition (2008) pp. 1-8.

Newman, J. et al., "Phase Behavior of Synthetic N-Acylethanolamine Phospholipids" Chemistry and Physics of Lipids. 42 (1986) pp. 249-260.

Swamy, M. et al., "Administration of a dietary supplement ( N-oleyl-phosphatidylethanolamine and epigallocatechin-3-gallate formula) enhances compliance with diet in healthy overweight subjects: a randomized controlled trial" Biophysic Journal, vol. 73, 1997, pp. 2556-2564.

Cardillo, R. et al., "A Simple Assay for the Quantitative Evaluation of Phospholipase D Activity" Biotechnology Techniques, 1985, vol. 7, No. 11, 795-798.

Bomstein, R. et al., "A New Class of Phosphatides Isolated from Soft Wheat Flour" Biochemical and Biophysical Research Communications, vol. 21, No. 1, 1965, pp. 49-54.

Clarke, N. et al., "Novel Lipids of Butyrivibrio SPP" Chemistry and Physics of Lipids, 17 (1976), pp. 222-232.

Kovatchev, S. et al., "The Preparation of Phospholipids by Phospholipase D" Advances in experimental medicine and biology, 101, 1978, pp. 221-226.

*Primary Examiner* — Kristin Bianchi
(74) *Attorney, Agent, or Firm* — Lucas & Mercanti, LLP

(57) ABSTRACT

The document describes a process for the preparation of N-Acyl-Phosphatidyl-Ethanolamine of formula (I) on an industrial scale, In which $R_1$, $R_2$ and $R_3$ are, independently from each other, saturated, monounsaturated or polyunsaturated acyls $C_{10}$-$C_{30}$, pure or mixed together, and X═OH or OM, where M=alkaline metal or alkaline earth, ammonium or alkylammonium. The process in question allows the conversion of lecithin of synthetic or natural origin into N-Acyl-Phosphatidyl-Ethanolamine of formula (I) of high purity, using a limited molar excess of the reagent N-acyl-ethanolamine, where the acyl is as defined above for the formula (I) through reaction of transphosphatidylation in the presence of the enzyme phospholipase D and in conditions suitable for production on an industrial scale.

(I)

$OR_1$
$OR_2$
O
$NHR_3$
O═P—O
X

27 Claims, No Drawings

PROCESS FOR THE PRODUCTION OF N-ACYL-PHOSPHATIDYL-ETHANOLAMINE

This application is a U.S. national stage of PCT/IT2008/000460 filed on Jul. 8, 2008, the content of which is incorporated herein by reference.

The object of the present invention is a process for the preparation of N-Acyl-Phosphatidyl-Ethanolimine of formula (I) on an industrial scale

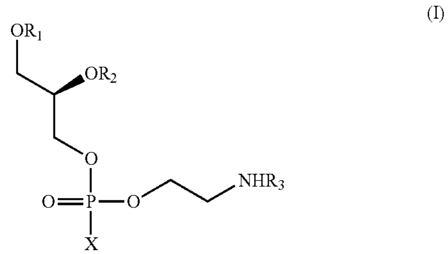

in which $R_1$, $R_2$ and $R_3$ are, independently from each other, saturated, monounsaturated or polyunsaturated acyls $C_{10}$-$C_{30}$, pure or mixed together, and X═OH or OM, where M=alkaline metal or alkaline earth, ammonium or alkylammonium.

The process object of the present invention allows the conversion of lecithin of synthetic or natural origin into N-Acyl-Phosphatidyl-Ethanolamine of formula (I) of high purity, using a limited molar excess of the reagent N-Acyl-Ethanolamine, where the acyl is as defined above for formula (I) through reaction of transphosphatidylation in the presence of the enzyme phospholipase D and in conditions suitable for production on an industrial scale.

FIELD OF THE INVENTION

The N-Acyl-Phosphatidyl-Ethanolamines (hereafter also known as "NAPE") are natural phospholipids present as minor elements of the lipid mixtures extracted from biological tissues.

Originally identified in wheat flour (Bomstein, R. A. Biochem. Biophys. Res. Commun. (1965) 21 49) they are present in products of vegetable origin, representing about 2% of the polar lipids contained in soy lecithin, and in micro-organisms (Clarke et al. Chem. Phys. Lipids (1976) 17 222).

The interest in NAPEs is continually developing both in terms of studies and their role in nature, for example as precursors of ligands for cannabinoid receptors (anandamide), and for use as cholesterol-reducers (cf. for example patent U.S. Pat. No. 4,254,115), anorectics (cf. for example patent application WO03068210). They are also used as main components of liposomial formulations (cf. patent U.S. Pat. No. 6,294,191) and as antioxidants.

The isolation of NAPEs from raw materials of natural origin is penalised by the low percentage of NAPE present and by the difficulty of separation from the other components of the lipid extracts. Consequently, in order to use NAPEs in the required applications, it is preferred to separate them from Phosphatidylethanolamine (hereafter called PE) according to the following scheme I.

SCHEME I

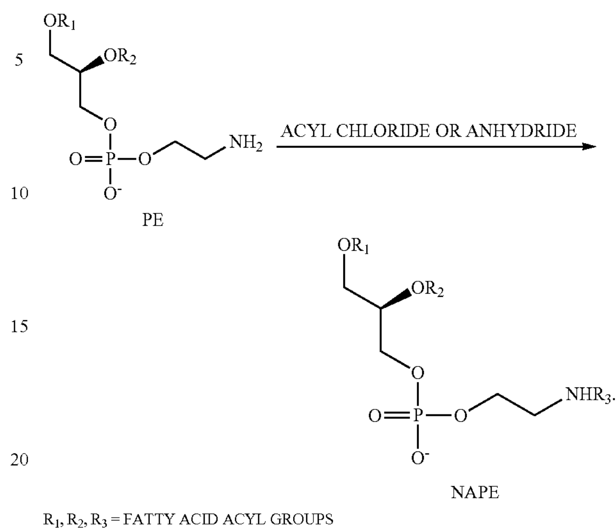

This synthesis allows NAPE to be obtained in which the acyl group bound to the nitrogen is defined, but it implies the use of PE that is expensive and has low commercial availability.

U.S. Pat. No. 4,783,402 describes the possibility of converting Phosphatidylcholine (PC) into a variety of products, including NAPEs, making use of a new enzyme known as Phospholipase DM, still not making any reference to the yields of the reactions. The experimental conditions shown in this patent do not lend themselves to use on an industrial scale, since they foresee that the reaction be carried out with high dilution of the substrate in a mixture of solvents comprising ethyl ether. Moreover, before the reaction the starting substrate (PC) is subjected to sonication to be emulsified.

In the transphosphatidylation reaction illustrated in scheme the enzyme phospholipase D promotes the exchange between different alcohol groups that esterify the phosphate group in the polar head of the phospholipids.

SCHEME II

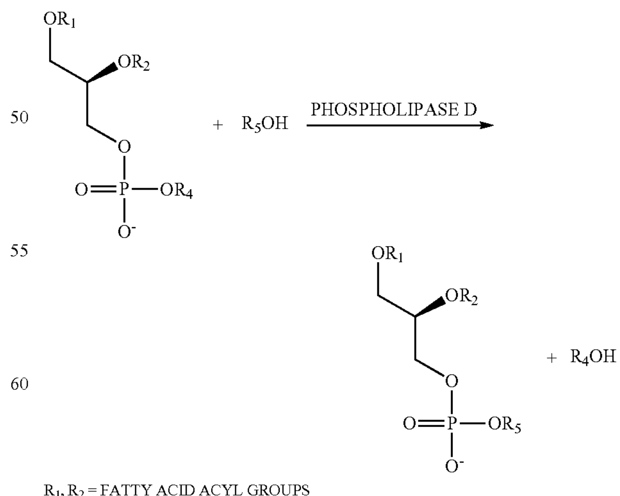

This conversion has proven very useful for the production, even on an industrial scale, of phospholipids of great pharmaceutical and nutritional interest. The transformation reactions of PC into PhosphatidylSerine, PhosphatidylGlycerol and PhosphatidylEthanolamine using the alcoholic reagents Serine, Glycerol and Ethanolamine, respectively, are well documented.

Patent application EP1048738 describes the transformation of lecithin of different origin into PhosphatidylSerine through transphosphatidylation with Serine in the presence of Phospholipase D. In this application, to promote transphosphatidylation reaction with respect to the competitive hydrolysis reaction an amount of Serine with respect to the phospholipid substrate of at least 4 moles/mole was used.

DESCRIPTION OF THE INVENTION

There is currently a need for a method that, overcoming the drawbacks described above, allows the production of NAPE in the amounts and with the degree of purity required by the, market from raw materials that are widely available and inexpensive.

The object of the present invention is therefore represented by a process for the preparation of N-Acyl-Phosphatidyl-Ethanolamine of formula (I)

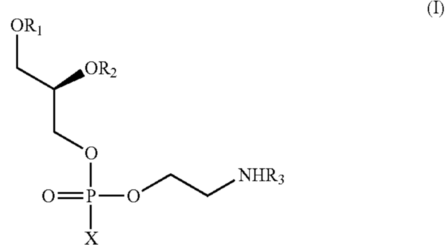

where $R_1$, $R_2$ and $R_3$ are, independently from each other, saturated, monounsaturated and/or polyunsaturated acyls $C_{10}$-$C_{30}$, X═OH or else OM, M=alkaline metal, alkaline earth, ammonium or else alkylammonium, comprising the reaction of phosphatides of formula (II),

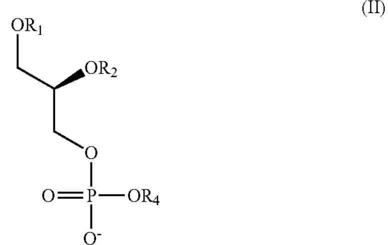

where $R_1$ and $R_2$ have the same meanings defined previously, and $R_4$═$CH_2$—$CH_2$—$N^+(CH_3)_3$ and/or $CH_2$—$CH_2$—$NH_3^+$, with a compound of formula (III),

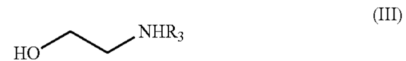

where $R_3$ has the same meaning defined previously, in the presence of phospholipase D, characterised in that said reaction is carried out in water or else in a mixture of water and at least one hydrocarbon.

According to an aspect of the invention, the molar ratio between compound of formula (III) and phosphatide of formula (II) is preferably less than 4, even more preferably between 1 and 3.

According to a further aspect of the invention, $R_1$, $R_2$ and/or $R_3$ are preferably acyls $C_{12}$-$C_{24}$; even more preferably, $R_3$ is selected from oleoyl, palmitoyl and arachidoyl. The process object of the present invention allows the conversion of lecithin of synthetic or natural origin into NAPE of formula (I) of high purity, using a limited molar excess of the reagent N-Acil-Ethanolamine, where the acyl is as defined above for formula (I) through transphosphatidylation reaction in the presence of the enzyme Phospholipase D and in conditions suitable for production on an industrial scale.

The alcoholic species participating in the transphosphatidylation reactions described in the prior art (serine, glycerol and ethanolamine) are characterised by a high solubility in water, whereas the ethanolamines acylated with fatty acids, which are the alcoholic species participating in the transphosphatidylation reaction object of the present invention, are compounds that are barely soluble in water. Said alcoholic species, moreover, have molecular structures containing at least twelve carbon atoms, and it is known that alcohols with aliphatic chains consisting of more than six carbon atoms have little potential for participating in the transphosphatidylation reaction (cf. Adv. Exp. Med. Biol. (1978) 101 221).

Despite these unfavourable conditions, we have surprisingly found that it is possible to carry out the transphosphatidylation reaction of synthetic and natural lecithins to give NAPE in conditions that lend themselves to production on an industrial scale.

The production of NAPEs through the process object of the present invention is particularly attractive considering the wide availability of the raw materials needed and the simplicity of the synthesis scheme.

Scheme III illustrates the synthesis of N-Oleoyl-PhosphatidylEthanolamine (hereafter also called "NOPE"), according to the process of the invention.

SCHEME III

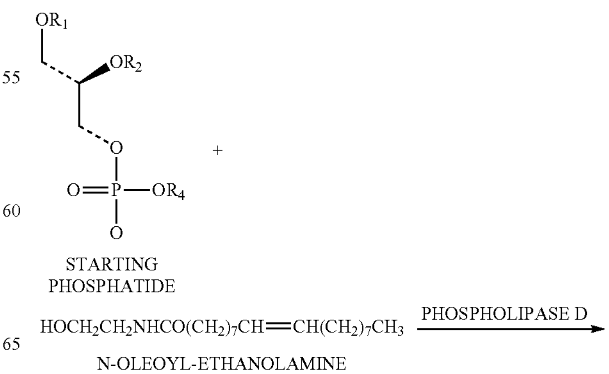

-continued

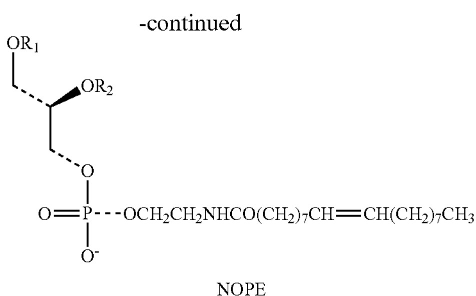

NOPE where $R_1$, $R_2$ and $R_4$ have the same meanings defined previously.

Surprisingly, it has been found that, through the process according to the present invention, a very high conversion of the starting lecithin into the end NAPE is obtained. It has also been found that, in such conditions, the competitive hydrolysis that leads to the formation of phosphatidic acid occurs in a practically negligible manner. Therefore, it was possible to carry out the transphosphatidylation reaction using a molar ratio of less than 3 moles of N-Acil-Ethanolamines per mole of phospholipid provided to react, consequently avoiding the large molar excesses that are used to limit the formation of phosphatidic acid in transphosphatidylations on an industrial scale.

An interesting feature of the present invention is represented by the fact that, whilst using inexpensive and widely available raw materials, such as fluid lecithins with a Phosphatidylcholine (PC) content limited even to low values like 30-35%, high purity NAPEs are obtained, which can be isolated by using simple processes that adapt well to implementation on an industrial scale of production. The $^{31}$P-NMR measurements show, indeed, that the purity and the content of the products obtained by following the teachings of the present invention are typically above 85%.

The transphosphatidylation reaction object of the present invention is carried out in a medium consisting of an aqueous component, consisting of an aqueous buffer and an optional organic component, consisting of a hydrocarbon solvent.

In order to carry out the invention the relative amounts of these components must respect clearly defined ranges, just as the ratio between such components and the amount of substrate constituting the raw material of the process must be controlled. In particular, the amount of hydrocarbon solvent is preferably less than 1 liter/liter of water and, even more preferably, it is between 0.3 and 0.7 liters/liter of water. It has been noted that when this ratio is between 0.3 and 0.7 liters/liter, the formation of phosphatidic acid is so low as to be less than the sensitivity (0.2%) of the analytic method used ($^{31}$P-NMR).

Moreover, the total amount of solvents (sum of the water and the optional hydrocarbon solvent) present in reaction with respect to the amount of phosphatide provided to react is preferably between 5 and 40 liters per kg of phosphatide, even more preferably between 6 and 20 liters.

The possibility of carrying out an effective transphosphatidylation reaction in accordance with the present invention is totally surprising, considering that in the aqueous phase in which there is the enzyme Phospholipase D neither the phospholipid substrate nor the reagent alcohol are dissolved. Indeed, the phospholipid substrate is dispersed in the aqueous phase, and the reagent alcohol is also dispersed in the aqueous phase or is present in the hydrocarbon solvent, when optionally used. Otherwise, in the more fully described cases of transphosphatidylation, the reagent alcohol is dissolved in the same aqueous phase in which the enzyme Phospholipase D is also present, thus making it likely for it to be easier for it to participate in the reaction.

By operating in these conditions it has been found that the reaction is surprisingly fast and selective leading to the almost complete conversion of the phosphatide in reaction times of less than 6 hours: the $^{31}$P-NMR analyses show a presence of residual PC of less than 3%, and concomitant formation of the hydrolysis product (Phosphatidic acid).

This last aspect of the invention is particularly relevant considering the known difficulty in separating the phosphatidic acid from the other phospholipids: avoiding its formation during the course of the reaction is therefore substantially advantageous for the subsequent purification of the NAPE.

The phospholipids that can be used as raw materials in the process of the present invention are natural lecithin of vegetable origin (like soy and sunflower) or of animal origin (like egg, krill, fish and fish eggs). Mixtures of phospholipids able to be obtained from the fermentation of monocellular species can also be advantageously used as substrates in this process.

Such lecithins can be of different degrees of purity and have a phosphatidylcholine content of below 50% by weight.

According to an aspect of the invention, phosphatides of formula (II) are mixtures of phosphatides of natural origin having a phosphatidylcholine and/or phosphatidylethanolamine content of between 20 and 95% by weight; the process of the present invention can advantageously also be carried out using mixtures of phosphatides of natural origin having a phosphatidylcholine and/or phosphatidylethanolamine content of between 25 and 45% by weight.

In order to obtain NAPE with defined composition of the fatty acids synthetic phosphatides can also be used, like for example 1,2-dioleoylphosphatidylcholine (DOPC), 1-palmitoyl-2-oleoylphosphatidylcholine (POPC), 1,2-dimiristoylphosphatidylcholine, (DMPC).

The N-Acil-ethanolamines able to be used can be of different origins, they can have different degrees of purity; the acyl group can derive from carboxylic acids containing from 10 to 30 carbon atoms, present individually or mixed together. Such acids can be saturated, unsaturated or polyunsaturated fatty acids. In particular, the arachidonic, palmitic and oleic acids are preferred.

For the hydrocarbon solvents it is possible to advantageously use both aromatic and aliphatic solvents, preferably having from 4 to 10 carbon atoms, even more preferably from 6 to 8 carbon atoms; more advantageously toluene or n-heptane are used.

The transphosphatidylation reaction can be carried out at temperatures of between 20 and 70° C., preferably between 30 and 50° C. The pH of the reaction can vary according to the origin of the enzyme used and preferably falls within the range between 3.5 and 9, even more preferably between 4 and 5.5.

The type of agitation influences the reaction speed and can advantageously be carried out through mechanical agitation, optionally magnetic. The aqueous reaction phase preferably consists of a buffer with a concentration of between 0.01 M and 0.2 M. Different types of buffer can be used, and preferably the buffer acetate is used.

The presence of divalent metallic ions, like for example calcium or magnesium, promotes the transphosphatidylation reaction catalysed by the phospholipase D; such ions are preferably used in the form of salts or else oxides; even more preferably, the reaction is carried out in the presence of calcium chloride. The concentration of said divalent metallic ions preferably falls within the range of between 0.05 and 0.5 M.

To carry out the reaction it is advantageous to select a phospholipase D enzyme that displays high transphosphatidylation activity compared to hydrolytic activity. Such an enzyme does not necessarily have to be purified. It is advantageously possible to use an enzyme of fermented origin, preferably produced from strains of the genus *Streptomyces*, like the one obtained by fermentation of the micro-organism filed as ATCC55717.

The amount of enzyme preferably falls within the range of between 10 and 100 units per gram of phospholipid provided to react. The enzyme activity is determined with the method described in Biotechn. Techn. (1993) 7 795).

As shall become clear from the examples, when the reaction mixture consists of water and at least one hydrocarbon, it is normally obtained by combining a buffered aqueous dispersion containing phosphatide of formula (II) with a hydrocarbon solution or dispersion of the compound of formula (III); the phospholipase D can already be present in the buffered aqueous dispersion containing the phosphatide of formula (II), or else it can be added at a later stage to the reaction mixture already formed. Alternatively, the reaction can be carried out in a buffered aqueous dispersion containing the phosphatide of formula (II), the compound of formula (III), and the phospholipase D.

In order to isolate the NAPEs it is advantageously possible to use processes known to the man skilled in the art such as liquid/liquid extractions and precipitation from acetone.

The following examples have to sole purpose of illustrating some ways of carrying out the invention and must not in any way be taken to be limiting.

EXAMPLE 1

75 g Phosal 35®, a fluid soy lecithin produced by Phospholipids GmbH with PC content equal to 35%, are loaded under agitation into a 1 L flask containing 750 mL of Acetone. The supernatant is removed and 320 mL of an acetate buffer 0.1 M pH=4.5 containing 10 g of calcium chloride are added into the flask. The residual acetone is removed by evaporation at low pressure. The mixture is heated to 43° C. and kept 30 minutes under agitation. Maintaining temperature and agitation a solution of 31 g N-Oleoyl-ethanolamine in 140 mL n-Heptane and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 86.8% NAPE and 1.4% PC. The PA is below the detection limit (0.2%).

EXAMPLE 2

28 g Phospholipon 90®, a soy lecithin produced by Phospholipids GmbH with PC content equal to 95%, are loaded into a 1 L flask with 320 mL of an acetate buffer 0.1 M pH=4.5 containing 10 g of calcium chloride. The mixture is heated to 43° C. and kept 60 minutes under agitation. Maintaining temperature and agitation a solution of 31 g N-Oleoyl-ethanolamine in 140 mL n-Heptane and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 94.9% NAPE and 0.9% PC. The PA is below the detection limit (0.2%).

EXAMPLE 3

28 g 1-Palmitoyl-2-Oleoyl-sn-Glycero-3-PhosphoCholine (POPC), a synthesis phospholipid produced by Chemi SpA, are loaded into a 1 L flask with 320 mL of an acetate buffer 0.1 M pH=4.5 containing 10 g of calcium chloride. The residual acetone is removed by evaporation at low pressure. The mixture is heated to 43° C. and kept 60 minutes under agitation. Maintaining temperature and agitation a solution of 31 g N-Oleoyl-ethanolamine in 140 mL n-Heptane and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 94.4% NAPE and 1.9% PC. The PA is below the detection limit (0.2%).

EXAMPLE 4

75 g Phosal 35®, a fluid soy lecithin produced by Phospholipids GmbH with PC content equal to 35%, are loaded under agitation into a 1 L flask containing 750 mL of Acetone. The supernatant is removed and 320 mL of an acetate buffer 0.1 M pH=4.5 containing 10 g of calcium chloride are added into the flask. The residual acetone is removed by evaporation at low pressure. The mixture is heated to 43° C. and kept 30 minutes under agitation. Maintaining temperature and agitation 31 g N-Oleoyl-ethanolamine and then a suspension of 0.75 g Phospholipase D from ATCC 55717 (specific activity 3200 U/g) in 20 mL of the same buffer are added in small portions.

The mixture is kept at the temperature for 5 hours with mechanical agitation. It is cooled to room temperature and a sample of the reaction product is taken analysing it with NMR.

The $^{31}$P-NMR spectrum shows the presence of 85.5% NAPE, 3.9% PC and 1.3% PA.

EXAMPLE 5

75 g Phosal 35®, a fluid soy lecithin produced by Phospholipids GmbH with PC content equal to 35%, are loaded under agitation into a 1 L flask containing 750 mL of Acetone. The supernatant is removed and 320 mL of an acetate buffer 0.1 M pH=4.5 containing 10 g of calcium chloride are added into the flask. The residual acetone is removed by evaporation at low pressure. The mixture is heated to 43° C. and kept 30 minutes under agitation. Maintaining temperature and agitation a solution of 31 g N-Oleoyl-ethanolamine in 140 mL of toluene and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 86.2% NAPE and 1.6% PC. The PA is below the detection limit (0.2%).

EXAMPLE 6

75 g Phosal 35®, a fluid soy lecithin produced by Phospholipids GmbH with PC content equal to 35%, are loaded under agitation into a 1 L flask containing 750 mL of Acetone. The supernatant is removed and 320 mL of an acetate buffer 0.1 M pH=4.5 containing 10 g of calcium chloride are added into the flask. The residual acetone is removed by evaporation at low pressure. The mixture is heated to 43° C. and kept 30 minutes under agitation. Maintaining temperature and agitation a solution of 31 g N-Oleoyl-ethanolamine in 140 mL n-Heptane and then a suspension of 0.28 g Phospholipase D produced by the company Yakult (specific activity 8500 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 85.2% NAPE and 2.4% PC. The PA is below the detection limit (0.2%).

EXAMPLE 7

75 g Phosal 35®, a fluid soy lecithin produced by Phospholipids GmbH with PC content equal to 35%, are loaded under agitation into a 1 L flask containing 750 mL of Acetone. The supernatant is removed and 320 mL of an acetate buffer 0.1 M pH=4.5 containing 10 g of calcium chloride are added into the flask. The residual acetone is removed by evaporation at low pressure. The mixture is heated to 43° C. and kept 30 minutes under agitation. Maintaining temperature and agitation a solution of 29 g N-Palmitoyl-ethanolamine in 230 mL n-Heptane and then a suspension of 0.75 g Phospholipase D from ATCC 55717 (specific activity 3200 U/g) in 20 mL of the same buffer are added.

The mixture is kept at the temperature for 6 ore with mechanical agitation. It is cooled to room temperature and a sample of the reaction product is taken analysing it with NMR.

The $^{31}$P-NMR spectrum shows the presence of 85.2% NAPE and 2.8% PC. The PA is below the detection limit (0.2%).

EXAMPLE 8

75 g Phosal 35®, a fluid soy lecithin produced by Phospholipids GmbH with PC content equal to 35%, are loaded under agitation into a 1 L flask containing 750 mL of Acetone. The supernatant is removed and 150 mL of an acetate buffer 0.1 M pH=4.5 containing 5 g of calcium chloride are added into the flask. The residual acetone is removed by evaporation at low pressure. The mixture is heated to 43° C. and kept 30 minutes under agitation. Maintaining temperature and agitation a solution of 31 g N-Oleoyl-ethanolamine in 310 mL n-Heptane and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 38.6% NAPE, 44.7% PC and 1.3% PA.

EXAMPLE 9

75 g Phosal 35®, a fluid soy lecithin produced by Phospholipids GmbH with PC content equal to 35%, are loaded under agitation into a 1 L flask containing 750 mL of Acetone. The supernatant is removed and 60 mL of an acetate buffer 0.1 M pH=4.5 containing 2 g of calcium chloride are added into the flask. The residual acetone is removed by evaporation at low pressure. The mixture is heated to 43° C. and kept 30 minutes under agitation. Maintaining temperature and agitation 31 g N-Oleoyi-ethanolamine in 30 mL n-Heptane and then a suspension of 0.75 g Phospholipase D from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 34.3% NAPE, 49.7% PC and 1.3% PA.

EXAMPLE 10

75 g Phosal 35®, a fluid soy lecithin produced by Phospholipids GmbH with PC content equal to 35%, are loaded under agitation into a 2 L flask containing 750 mL of Acetone. The supernatant is removed and 1.2 L of an acetate buffer 0.1 M pH=4.5 containing 35 g of calcium chloride are added into the flask. The residual acetone is removed by evaporation at low pressure. The mixture is heated to 43° C. and kept 30 minutes under agitation. Maintaining temperature and agitation a solution of 31 g N-Oleoyl-ethanolamine in 560 mL n-Heptane and then a suspension of 0.75 g Phospholipase from ATCC 55717 (specific activity 3200 U/g) in 20 mL of the same buffer are added.

The mixture is kept at the temperature for 5 hours with mechanical agitation. It is cooled to room temperature and a sample of the reaction product is taken analysing it with NMR.

The $^{31}$P-NMR spectrum shows the presence of 83.2% NAPE, 4.6% PC and 2.6% PA.

The invention claimed is:

1. A process for the preparation of N-Acyl-Phosphatidyl-Ethanolamine of formula (I)

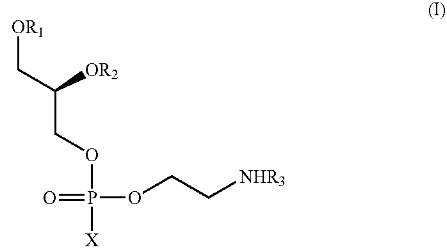

where $R_1$, $R_2$ and $R_3$ are, independently from each other, saturated, monounsaturated and/or polyunsaturated acyls $C_{10}$-$C_{30}$, X=OH or OM, M=alkaline metal, alkaline earth, ammonium or alkylammonium, comprising reacting phosphatides of formula (II),

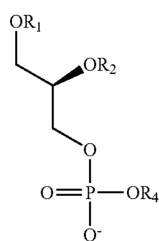

where $R_1$ and $R_2$ have the same meanings defined previously, and $R_4$=$CH_2$—$CH_2$—$N^+(CH_3)_3$ and/or $CH_2$—$CH_2$—$NH_3^+$, with a compound of formula (III),

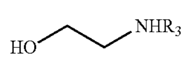

where $R_3$ has the same meaning defined previously, in the presence of phospholipase D, wherein said reaction is carried out in water or in a mixture of water and at least one hydrocarbon.

2. Process according to claim 1, wherein said mixture of water and at least one hydrocarbon is obtained by combining a buffered aqueous dispersion containing the phosphatide of formula (II) with a hydrocarbon solution or dispersion of the compound of formula (III).

3. Process according to claim 1, wherein said reaction is carried out in a buffered aqueous dispersion containing the phosphatide of formula (II) and the compound of formula (III).

4. Process according to claim 1, wherein the molar ratio between compound of formula (III) and phosphatide of formula (II) is less than 4.

5. Process according to claim 4, wherein the molar ratio between compound of formula (III) and phosphatide of formula (II) is between 1 and 3.

6. Process according to claim 1, wherein $R_1$, $R_2$ and/or $R_3$ are acyls $C_{12}$-$C_{24}$.

7. Process according to claim 6, $R_3$ is selected from oleoyl, palmitoyl and arachidoyl.

8. Process according to claim 1, wherein the water is buffered at a pH of between 3.5 and 9.

9. Process according to claim 1, wherein said process is carried out in the presence of calcium and/or magnesium ions.

10. Process according to claim 1, wherein said phospholipase D is of fermented origin.

11. Process according to claim 10, wherein said phospholipase D is produced from strains of the genus *Streptomyces*.

12. Process according to claim 1, wherein said phosphatides of formula (II) are mixtures of phosphatides of natural origin having a phosphatidylcholine and/or ethanolamine content of between 20% and 95% by weight.

13. Process according to claim 12, wherein said phosphatides of formula (II) are mixtures of phosphatides of natural origin having a phosphatidylcholine and/or ethanolamine content of between 25% and 45% by weight.

14. Process according to claim 1, wherein said phosphatides of formula (II) are lecithins having a phosphatidylcholine content of less than 50% by weight.

15. Process according to claim 1, wherein said phosphatides of formula (II) are soy and/or egg lecithins.

16. Process according to claim 1, wherein said phosphatide of formula (II) is a phosphatide of synthetic origin.

17. Process according to claim 1, wherein said hydrocarbon is a hydrocarbon $C_4$-$C_{10}$, preferably.

18. Process according to claim 17, wherein said hydrocarbon is selected from toluene and n-heptane.

19. Process according to claim 1, wherein said hydrocarbon is present in an amount of less than 1 liter/liter of water.

20. Process according to claim 19, wherein said hydrocarbon is present in an amount of between 0.3 and 0.7 liters/liter of water.

21. Process according to claim 1, wherein the water and the hydrocarbon solvent are present in an overall amount of between 5 and 40 liters/Kg of phosphatide of formula (II).

22. Process according to claim 1, wherein said process is carried out at a temperature of between 20 and 70° C.

23. Process according to claim 1, wherein said process is carried out without the addition of surfactants and/or sonication.

24. Process according to claim 1, wherein the water is buffered at a pH of between 4 and 5.5.

25. Process according to claim 16, wherein said phosphatide is 1,2-dioleoylphosphatidylcholine (DOPC), 1-palmitoyl-2-oleoylphosphatidylcholine (POPC) or 1,2-dimiristoylphosphatidylchloline (DMPC).

26. Process according to claim 21, wherein the water and the hydrocarbon solvent are present in an amount of between 6 and 20 liters/Kg of phosphatide.

27. Process according to claim 1, wherein said process is carried out at a temperature of between 30 and 50° C.

* * * * *